(12) United States Patent
Sun et al.

(10) Patent No.: US 6,518,218 B1
(45) Date of Patent: Feb. 11, 2003

(54) CATALYST SYSTEM FOR PRODUCING CARBON FIBRILS

(75) Inventors: Xiao-Dong Sun, Schenectady, NY (US); Navjot Singh, Clifton Park, NY (US); Lionel Monty Levinson, Schenectady, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 09/535,811

(22) Filed: Mar. 28, 2000

Related U.S. Application Data
(60) Provisional application No. 60/127,038, filed on Mar. 31, 1999.

(51) Int. Cl.$^7$ ............................ B01J 21/06; B01J 23/26; B01J 23/72; B01J 23/745; B01J 23/753
(52) U.S. Cl. ................ 502/259; 502/302; 502/305; 502/306; 502/307; 502/313; 502/314; 502/315; 502/316; 502/319; 502/320; 502/321; 502/322; 502/323; 502/325; 502/328; 502/329; 502/332; 502/335; 502/336; 502/337; 502/338; 502/340; 502/341; 502/342; 502/343; 502/262; 502/232; 502/240; 502/244; 502/245; 502/254; 502/255; 502/256; 502/257; 502/258; 502/261; 502/263
(58) Field of Search .......................... 502/302, 305, 502/306, 307, 313, 314, 315, 316, 319, 320, 321, 322, 323, 325, 328, 329, 332, 335, 336, 337, 338, 340, 341, 342, 343, 262, 232, 240, 244, 245, 254, 255, 256, 257, 258, 259, 261, 263

(56) References Cited

U.S. PATENT DOCUMENTS

| | | | | |
|---|---|---|---|---|
| 4,001,317 A | * | 1/1977 | Grasselli et al. | ............ 502/304 |
| 4,497,788 A | | 2/1985 | Bradley et al. | |
| 4,518,575 A | | 5/1985 | Porter et al. | |
| 4,970,123 A | | 11/1990 | Witzke et al. | |
| 4,985,387 A | * | 1/1991 | Pringent et al. | ............ 502/304 |
| 5,149,584 A | | 9/1992 | Baker et al. | |
| 5,182,249 A | * | 1/1993 | Wang et al. | ................ 502/303 |
| 5,597,611 A | | 1/1997 | Lennox et al. | |
| 5,643,670 A | * | 7/1997 | Chung | ........................ 427/115 |
| 5,643,990 A | | 7/1997 | Uehara et al. | |
| 5,935,898 A | * | 8/1999 | Trubenbach et al. | ........ 502/300 |
| 5,981,427 A | * | 11/1999 | Sung et al. | ................. 502/325 |
| 6,235,674 B1 | * | 5/2001 | Tennent et al. | .......... 423/447.1 |

FOREIGN PATENT DOCUMENTS

| | | |
|---|---|---|
| WO | 9007023 | 12/1989 |
| WO | 9304119 | 8/1992 |

OTHER PUBLICATIONS

"Formation and Texture of Carbon Nanofilaments by the Catalytic Decomposition of CO on Stainless–Steel Plate", Y. Soneda, M. Makino, Letters to the Editor 1 Carbon 38, (2000), pps. 478–480.

"Carbon Single Wall Nanotubes Elaboration and Properties", P. Bernier, W. Maser, C. Journet, A. Loiseau, M. Lamy Dela Chappell, S. Lefrant, R. Lee and J.E. Fischer, Carbon, vol. 36, No. 5. pps. 675–680, 1998.

* cited by examiner

*Primary Examiner*—Elizabeth D. Wood
(74) *Attorney, Agent, or Firm*—Bernadette M. Bennett; Noreen C. Johnson

(57) ABSTRACT

A catalyst system and method for making carbon fibrils is provided which comprises a catalytic amount of an inorganic catalyst comprising nickel and one of the following substances selected from the group consisting of chromium; chromium and iron; chromium and molybdenum; chromium, molybdenum, and iron; aluminum; yttrium and iron; yttrium, iron and aluminum; zinc; copper; yttrium; yttrium and chromium; and yttrium, chromium and zinc. In a further aspect of the invention, a catalyst system and method is provided for making carbon fibrils which comprises a catalytic amount of an inorganic catalyst comprising cobalt and one of the following substances selected from the group consisting of chromium; aluminum; zinc; copper; copper and zinc; copper, zinc, and chromium; copper and iron; copper, iron, and aluminum; copper and nickel; and yttrium, nickel and copper.

14 Claims, No Drawings

CATALYST SYSTEM FOR PRODUCING CARBON FIBRILS

CROSS REFERENCE TO RELATED APPLICATIONS

This application claims priority from Provisional Application No. 60/127,038 entitled "New Catalysts for Synthesis of Carbon Fibrils," filed on Mar. 31, 1999 which is incorporated herein by reference.

BACKGROUND OF THE INVENTION

The present invention is related to a catalyst system for preparing carbon fibrils. More specifically, the invention is related to carbon fibrils and new catalysts which have been found useful for the synthesis of carbon fibrils.

Carbon fibrils, also known as carbon nanotubes, are microscopic fibers of carbon which are either tubes or dense fibers (i.e. not hollow) with a typical diameter in a range between about 1 nanometer and about 500 nanometers. In particular, it is often preferable to synthesize carbon fibrils with a diameter in a range between about 10 nanometers and about 50 nanometers. The aspect ratio of length of the carbon fibril to the diameter of the carbon fibril is typically greater than about 100.

Production of carbon fibrils is a well known synthetic process. They are typically synthesized using a catalytic vapor decomposition process, in which an organic vapor is flushed over dispersed metal catalysts at temperatures ranging from 400° C. to 1300° C. to form carbon fibrils. The chemical nature of the metal catalysts influences the yield and morphology of the synthesized carbon fibrils.

Mandeville et al. and Moy et al., U.S. Pat. Nos. 5,500,200 and 5,726,116 respectively, discuss the reaction of a source of carbon over a catalyst in a reaction system to produce carbon fibrils. However, Mandeville et al. and Moy et al. are ostensibly limited to iron catalysts and their binary alloys. In addition, these patents are not concerned with tertiary or quaternary combinations of catalysts which may have a synergistic effect compared to singular or binary combinations.

Due to the increasing interest in carbon fibrils, alternate catalysts that will result in the synthesis of carbon fibrils at high yield and high efficiency are constantly being sought.

BRIEF SUMMARY OF THE INVENTION

In one embodiment, the present invention provides a catalyst system for making carbon fibrils, the system comprising a catalytic amount of an inorganic catalyst comprising nickel and one of the following substances selected from the group consisting of:
chromium;
chromium and iron;
chromium and molybdenum;
chromium, molybdenum, and iron;
aluminum;
yttrium and iron;
yttrium, iron and aluminum;
zinc;
copper;
yttrium;
yttrium and chromium; and
yttrium, chromium and zinc.

A further aspect of the invention provides a catalyst system for making carbon fibrils, the system comprising a catalytic amount of an inorganic catalyst comprising cobalt and one of the following substances selected from the group consisting of:
chromium;
aluminum;
zinc;
copper;
copper and zinc;
copper, zinc, and chromium;
copper and iron;
copper, iron, and aluminum;
copper and nickel; and
yttrium, nickel and copper.

Yet another aspect of the present invention is a method for making carbon fibrils wherein the method comprises reacting a carbon source and a catalyst system. The catalyst system comprises an inorganic catalyst comprising nickel and one of the following substances selected from the group consisting of:
chromium;
chromium and iron;
chromium and molybdenum;
chromium, molybdenum, and iron;
aluminum;
yttrium and iron;
yttrium, iron and aluminum;
zinc;
copper;
yttrium;
yttrium and chromium; and
yttrium, chromium and zinc.

Yet a further aspect of the present invention is a method for making carbon fibrils wherein the method comprises reacting a carbon source and a catalyst system. The catalyst system comprises an inorganic catalyst comprising cobalt and one of the following substances selected from the group consisting of:
chromium;
aluminum;
zinc;
copper;
copper and zinc;
copper, zinc, and chromium;
copper and iron;
copper, iron, and aluminum;
copper and nickel; and
yttrium, nickel and copper.

DETAILED DESCRIPTION OF THE INVENTION

One aspect of the present invention is directed to new catalysts which successfully synthesize carbon fibrils have been discovered. The synthesis of carbon fibrils typically involves the reaction of a carbon source in the presence of an inorganic catalyst. In one embodiment of the present invention, the carbon fibrils are synthesized with a catalytic amount of a catalyst which includes nickel and at least one other substance. The catalyst may be substantially free of iron. "Substantially free" of iron as used herein refers to iron present in an amount less than 1% by weight of the total catalyst. In a second embodiment of the present invention, the carbon fibrils are synthesized with a catalytic amount of a catalyst which includes cobalt and at least one other substance. A "substance" as used herein refers to at least one metal, metal alloy, or combinations thereof with cobalt or nickel. "Catalytic amount" as used herein refers to an amount of catalyst sufficient to form carbon fibrils.

When the catalyst system is binary, the ratio of the metals, metal alloys, or mixtures thereof are typically in a range between about 10:1 and about 1:1. When the catalyst system is tertiary, the ratio of the metals, metal alloys, or mixtures thereof are typically in a range between about 10:10:1 and about 1:1:1. When the catalyst system is quaternary, the ratio of the metals, metal alloys or mixtures thereof are typically in a range between about 10:10:10:1 and about 1:1:1:1.

The catalyst, catalyst precursors or mixtures thereof are placed on a substrate. "Substrate" as used herein refers to any material which supports a collection of solid state materials (i.e. catalysts, catalyst precursors, or mixtures thereof). There is typically minimum interaction between the supported solid state materials and substrate material during chemical reaction or synthesis. However, certain substrates which have been found to be catalytic substances may have a synergistic effect on the production of carbon fibrils. Typical substrates include ceramics, for example, alumina; glass; metals, for example, aluminum, stainless steel, copper, silver, gold, platinum, and brass; and single crystals, for example, quartz, magnesium oxide, silicon, sapphire, and lanthanum aluminate.

The amount of catalysts placed on the substrate is typically in a range between nanograms and a few tens of milligrams. Typical total catalyst loading on the substrate is in a range between micrograms and a few grams, although with larger reactor size, the amount of catalysts loaded in a reactor may commonly be as much as a few pounds.

The catalysts may be deposited on the substrate sequentially or preferably, simultaneously. Catalysts may be deposited on a substrate using a gun sputtering deposition system. A gun sputtering deposition system contains elemental metal sources, metal alloy sources, or mixtures thereof placed in the gun cavity. An electrical discharge can be created at each source by applying radio frequency (RF) or direct current (DC) power in a range between about 10 Watts and about 1,000 Watts through the sputter gun, which heats the metal, metal alloy, or mixture thereof to form a metal plasma vapor. The metal vapor from the sputter gun is deposited onto a counter-facing substrate. The thickness of the material deposited is dependent upon several factors, including fixed power input. The amount of material deposited can be altered by changing the amount of time the sputter gun is pulsed.

Once the metal vapors have been deposited on the substrate, the catalysts are typically thermally annealed. The catalysts are heated to a temperature in a range between about 200° C. and about 1100° C., and preferably, to a temperature in a range between about 600° C. and about 800° C. During annealing, the catalysts are also typically in an environment to prevent the oxidation of the elemental metals or metal alloys. Examples of typical gases include argon, helium, nitrogen, hydrogen and mixtures thereof. Although the invention is not dependent upon theory, the temperature and atmospheric conditions may promote the interdiffusion and mixing of the combined metals to form catalysts.

An alternative manner for depositing a catalyst on a substrate is through the use of a liquid dispensing system. Each liquid dispenser is individually controlled and programmed to dispense a liquid material. The liquid dispensers are each filled with a soluble metal precursor such as a nitrate, acetate, and other aqueous soluble metal salt compound. The elemental metal, metal mixture, or mixtures thereof are carried in the soluble precursor. Once the soluble precursor comprising elemental metal, metal mixture, or mixtures thereof is deposited on the substrate as a liquid, the precursor is typically dried, calcined, and annealed (for example, in nitrogen, argon, helium, or mixtures thereof) to form an oxide-containing powder catalyst. To synthesize metal or alloy catalysts from such oxide-containing powders, reducing (for example, using hydrogen, charcoal, or carbon monoxide) in a time range between about 0.5 hours and about 12 hours at a temperature in a range between about 300° C. and about 800° C. is typically sufficient. By use of a soluble precursor, any oxidation of the inorganic metal or metal alloy is not a problem.

Once the above-mentioned catalysts are created, the catalysts may be used to synthesize carbon fibrils. The method commonly used to synthesize carbon fibrils may be a solid state reaction. The catalysts on the substrate are typically placed in a reaction chamber, such as a quartz tube reactor, at a temperature in a range between about 300° C. and about 1000° C., and preferably in a range between about 400° C. and about 700° C. The elevated temperature in the reactor facilitates the synthesis of the carbon fibrils.

The reactor can be operated under a pressure in a range between about 1 torr and about 100 atmospheres. The synthesis is typically run at a pressure in a range between about 100 torr and about 10 atmospheres.

In preferred embodiments, the reactor is filled with a gas in order to create a non-reactive atmosphere in the reaction chamber. In particular, the reactor is filled with a gas in order to create a non-oxidative environment such that the metal catalysts will not be oxidized. Commonly, there is a constant flow of gas. Examples of suitable gases include argon, helium, nitrogen, hydrogen, and mixtures thereof. Typically, argon and hydrogen are used and are present in a volume ratio in a range between about 5.5:1 and about 1:1. A mixture of argon and hydrogen is most commonly used at a volume ratio of 5:1 of argon to hydrogen. Due to the varying volume capacity of different reaction chambers, the flow rate can vary. Typically, the flow rate of the gas is such that it takes approximately 8 minutes to refresh the gas in the tube.

The reaction chamber is then filled with a steady flow of a carbon source, for example organic vapor, at the elevated reaction temperature. Typical organic vapors which can be used in the present invention include acetylene, ethylene, methane, benzene, carbon monoxide and mixtures thereof. Commonly, the organic vapor is mixed with one of the gases mentioned above. Typically, a combination of ethylene gas with hydrogen gas is used at a volume ratio of 5:1. When the organic vapor comes in contact with the catalyst, the organic vapor and catalyst react and carbon fibrils are synthesized. Carbon fibrils may also be synthesized from a reactant product of the gas and the organic vapor under the process conditions.

Depending on the reactivity of the catalysts, among other factors, the reaction time to synthesize carbon fibrils can be in a range between seconds and hours. With the reactor used in the present invention, the reaction time is typically in a range between about 10 minutes and about 8 hours.

The yields and morphology of the carbon fibrils are typically examined by standard techniques. These techniques include optical microscopy, scanning electron microscopy (SEM), transmission electron microscopy, X-ray diffraction, Raman scattering and laser profilometry. In addition, the electrical conductivity of the carbon fibrils formed is typically measured using a standard conductivity measurement, for example, a direct four point contact measurement.

The morphology of the carbon fibrils, after examination through scanning electron microscopy, are typically found to be either coiled or straight. In addition, the diameters of some of the carbon fibrils produced are typically found to be in a range of between about 1 nanometer and about 500 nanometers.

Carbon fibrils can be used for a variety of applications. Most typically, carbon fibrils are used as an additive in organic resins such as thermoplastic resin compositions or thermoset polymer compositions to impart particular physical properties. For example, carbon fibrils are used to make conductive composites with thermoplastic resins that can be used for electrostatic painting and electrostatic dissipation applications. The major constituent of the thermoplastic resin compositions is at least one thermoplastic polymer. Both addition and condensation polymers are included. Illustrative, non-limiting examples of thermoplastic polymers are olefin-derived polymers such as polyethylene, polypropylene, and their copolymers; polymethylpentane; diene-derived polymers such as polybutadiene, polyisoprene, and their copolymers; polymers of ethylenically unsaturated carboxylic acids and their functional derivatives, including acrylic polymers such as poly(alkyl acrylates), poly(alkyl methacrylates), polyacrylamides, polyacrylonitrile and polyacrylic acid; alkenylaromatic polymers such as polystyrene, poly-alpha-methylstyrene, polyvinyltoluene, and rubber-modified polystyrenes; polyamides such as nylon-6, nylon-66, nylon-11, and nylon-12; polyesters; polycarbonates; polyestercarbonates; polyethers such as polyarylene ethers, polyethersulfones, polyetherketones, polyetheretherketones, and polyetherimides; polyarylene sulfides, polysulfones, and polysulfidesulfones; and liquid crystalline polymers.

Both thermoplastic polyesters and thermoplastic elastomeric polyesters are suitable for use in the present invention. Illustrative, non-limiting examples of thermoplastic polyesters include poly(ethylene terephthalate), poly(1,4-butylene terephthalate), poly(1,3-propylene terephthalate), poly(cyclohexanedimethanol terephthalate), poly(cyclohexanedimethanol-co-ethylene terephthalate), poly(ethylene naphthalate), poly(butylene naphthalate), and polyarylates. Illustrative, non-limiting examples of thermoplastic elastomeric polyesters (commonly known as TPE) include polyetheresters such as poly(alkylene terephthalate)s (particularly poly[ethylene terephthalate] and poly[butylene terephthalate]) containing soft-block segments of poly(alkylene oxide), particularly segments of poly(ethylene oxide) and poly(butylene oxide); and polyesteramides such as those synthesized by the condensation of an aromatic diisocyanate with dicarboxylic acids and a carboxylic acid-terminated polyester or polyether prepolymer.

Suitable polyarylates include, but are not limited to, the polyphthalate esters of 2,2-bis(4-hydroxyphenyl)propane (commonly known as bisphenol A), and polyesters consisting of structural units of the formula II:

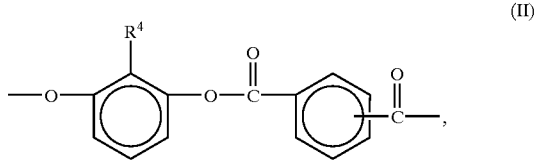

wherein $R^4$ is hydrogen or $C_{1-4}$ alkyl, optionally in combination with structural units of the formula III:

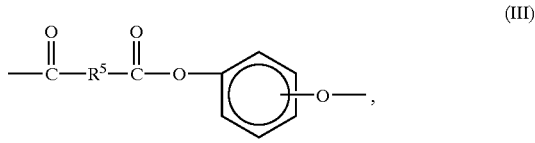

wherein $R^5$ is a divalent $C_{4-12}$ aliphatic, alicyclic or mixed aliphatic-alicyclic radical. The latter polyesters may be prepared by the reaction of a 1,3-dihydroxybenzene moiety with at least one aromatic dicarboxylic acid chloride under alkaline conditions. Structural units of formula II contain a 1,3-dihydroxybenzene moiety which may be substituted with halogen, usually chlorine or bromine, or preferably with $C_{1-4}$ alkyl; e.g., methyl, ethyl, isopropyl, propyl, butyl. Said alkyl groups are preferably primary or secondary groups, with methyl being more preferred, and are most often located in the ortho position to both oxygen atoms although other positions are also contemplated. The most preferred moieties are resorcinol moieties, in which $R^4$ is hydrogen. Said 1,3-dihydroxybenzene moieties are linked to aromatic dicarboxylic acid moieties which may be monocyclic moieties, e.g., isophthalate or terephthalate, or polycyclic moieties, e.g., naphthalenedicarboxylate. Preferably, the aromatic dicarboxylic acid moieties are isophthalate and/or terephthalate: either or both of said moieties may be present. For the most part, both are present in a molar ratio of isophthalate to terephthalate in a range between about 0.25 and about 4.0:1, preferably in a range between about 0.8 and about 2.5:1.

In the optional soft block units of formula II, resorcinol or alkylresorcinol moieties are again present in ester-forming combination with $R^5$ which is a divalent $C_{4-12}$ aliphatic, alicyclic or mixed aliphatic-alicyclic radical. It is preferably aliphatic and especially $C_{8-12}$ straight chain aliphatic. A particularly preferred arylate polymer containing soft block units is one consisting of resorcinol isophthalate and resorcinol sebacate units in a molar ratio in a range between about 8.5:1.5 and about 9.5:0.5.

Polycarbonates useful in the compositions of the invention include those comprising structural units of the formula IV:

wherein at least about 60 percent of the total number of $R^6$ groups are aromatic organic radicals and the balance thereof are aliphatic, alicyclic, or aromatic radicals. Suitable $R^6$ radicals include m-phenylene, p-phenylene, 4,4'-biphenylene, 4,4'-bi(3,5-dimethyl)-phenylene, 2,2-bis(4-phenylene)propane, 6,6'-(3,3,3', 3'-tetramethyl-1,1'-spirobi[1H-indan]), 1,1'-bis(4-phenylene)-3,3,5-trimethylcyclohexane, and similar radicals such as those which correspond to the dihydroxy-substituted aromatic hydrocarbons disclosed by name or formula (generic or specific) in U.S. Pat. No. 4,217,438.

More preferably, $R^6$ is an aromatic organic radical and still more preferably a radical of the formula V:

  (V)

wherein each $A^1$ and $A^2$ is a monocyclic divalent aryl radical and $Y^1$ is a bridging radical in which one or two atoms separate $A^1$ and $A^2$. For example, $A^1$ and $A^2$ typically represent unsubstituted phenylene or substituted derivatives thereof. The bridging radical $Y^1$ is most often a hydrocarbon group and particularly a saturated group such as methylene; cyclohexylidene, 3,3,5-trimethylcyclohexylidene; or isopropylidene. The most preferred polycarbonates are bisphenol A polycarbonates, in which each of $A^1$ and $A^2$ is p-phenylene and $Y^1$ is isopropylidene. Preferably, the weight average molecular weight of the initial polycarbonate is in a range between about 5,000 and about 100,000; more preferably in a range between about 10,000 and about 65,000, still more preferably in a range between about 16,000 and about 40,000, and most preferably in a range between about 20,000 and about 36,000. Suitable polycarbonates may be made using any process known in the art, including interfacial, solution, solid state, or melt processes.

In one embodiment the present invention comprises a composition containing at least one polycarbonate. In another embodiment the invention comprises compositions containing two different polycarbonates. Both homopolycarbonates derived from a single dihydroxy compound monomer and copolycarbonates derived from more than one dihydroxy compound monomer are encompassed.

Polyarylene ethers used in the present invention are most often polyphenylene ethers having structural units of the formula:

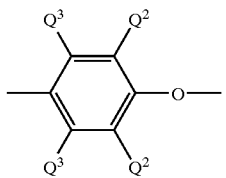

wherein each $Q^2$ is independently halogen, primary or secondary lower alkyl, phenyl, haloalkyl, aminoalkyl, hydrocarbonoxy, or halohydrocarbonoxy wherein at least two carbon atoms separate the halogen and oxygen atoms, and each $Q^3$ is independently hydrogen, halogen, primary or secondary lower alkyl, phenyl, haloalkyl, hydrocarbonoxy or alohydrocarbonoxy as defined for $Q^2$.

Both homopolymer and copolymer polyphenylene ethers are included. The preferred homopolymers are those containing 2,6-dimethyl-1,4-phenylene ether units. Suitable copolymers include random copolymers containing such units in combination with, for example, 2,3,6-trimethyl-1,4-phenylene ether units. Also included are polyphenylene ethers containing moieties prepared by grafting onto the polyphenylene ether in known manner such materials as vinyl monomers or polymers such as polystyrenes and elastomers, as well as coupled polyphenylene ethers in which coupling agents such as low molecular weight polycarbonates, quinones, heterocycles and formulas undergo reaction in known manner with the hydroxy groups of two polyphenylene ether chains to produce a higher molecular weight polymer.

The polyphenylene ethers generally have an intrinsic viscosity greater than about 0.1, most often in a range between about 0.2 deciliters per gram and about 0.6 deciliters per gram and especially about 0.35 deciliters per grams and about 0.6 deciliters per gram (dl./g.), as measured in chloroform at 25° C.

The polyphenylene ethers are typically prepared by the oxidative coupling of at least one monohydroxyaromatic compound such as 2,6-xylenol or 2,3,6-trimethylphenol. Catalyst systems are generally employed for such coupling; they typically contain at least one heavy metal compound such as a copper, manganese or cobalt compound, usually in combination with various other materials.

Particularly useful polyphenylene ethers are those which comprise molecules having at least one aminoalkyl-containing end group. The aminoalkyl radical is covalently bound to a carbon atom located in an ortho position to a hydroxy group. Products containing such end groups may be obtained by incorporating an appropriate primary or secondary monoamine such as di-n-butylamine or dimethylamine as on e of the constituents of the oxidative coupling reaction mixture. Also frequently present are 4-hydroxybiphenyl end groups and/or biphenyl structural units, typically obtained from reaction mixtures in which a by-product diphenoquinone is present, especially in a copper-halide-secondary or tertiary amine system. A substantial proportion of the polymer molecules, typically constituting as much as about 90% by weight of the polymer, may contain at least one of said aminoalkyl-containing and 4-hydroxy-biphenyl end groups. It will be apparent to those skilled in the art from the foregoing that the polyphenylene ethers contemplated f or use in the invention include all those presently known, irrespective of variations in structural units or ancillary chemical features.

Both homopolymer and copolymer thermoplastic polymers are included in the compositions of the present invention. Copolymers may include random, block or graft type. Thus, for example, suitable polystyrenes include homopolymers, such as amorphous polystyrene and syndiotactic polystyrene, and copolymers containing these species. The latter embraces high impact polystyrene (HIPS), a genus of rubber-modified polystyrenes comprising blends and grafts wherein the rubber is a polybutadiene or a rubbery copolymer of styrene in a range between about 70% by weight and about 98% by weight and diene monomer in a range between about 2% by weight and about 30% by weight. Also included are ABS copolymers, which are typically grafts of styrene and acrylonitrile on a previously formed diene polymer backbone (e.g., polybutadiene or polyisoprene). Suitable ABS copolymers may be produced by any methods known in the art. Especially preferred ABS copolymers are typically produced by mass polymerization (often referred to as bulk ABS) or emulsion polymerization (often referred to as high rubber graft ABS).

The preferred thermoplastic polymers for many purposes are polyesters, polycarbonates, polyphenylene ethers, polystyrene resin, high impact poly styrene resin (HIPS), and styrene-acrylonitrile co polymers (SAN), including ABS copolymers. These may be employed individually or as blends. Especially preferred blends include those of polyphenylene ether with at least one of HIPS, amorphous polystyrene, syndiotactic polystyrene, polyester, and polyamide; and polycarbonate blends with at least one of ABS, SAN, and polyester.

Illustrative, non-limiting examples of thermoset polymers include polymers derived from silicones, polyphenylene ethers, epoxys, cyanate esters, unsaturated polyesters, multifunctional allylic compounds such as diallylphthalate, acrylics, alkyds, phenol-formaldehyde, novolacs, resoles, bismaleimides, PMR resins, melamine-formaldehyde, urea-formaldehyde, benzocyclobutanes, hydroxymethylfurans, and isocyanates. In one embodiment of the present invention, the thermoset polymer further comprises at least one thermoplastic polymer, such as, but not limited to, polyphenylene ether, polyphenylene sulfide, polysulfone, polyetherimide, or polyester. The thermoplastic polymer is typically combined with a thermoset monomer mixture before curing of said thermoset.

Carbon fibrils are most often used as an additive with polyphenylene ether compositions and polycarbonate compositions. Carbon fibrils may be present in a range between about 0.01% by weight and about 20% by weight of the thermoplastic resin or mixture of resins and more commonly, in a range between about 0.1% by weight and about 7% by weight of the thermoplastic resin or mixtures of resins.

In order that those skilled in the art will be better able to practice the invention, the following examples are given by way of illustration and not by way of limitation.

EXAMPLE 1

Catalysts were fabricated with four metals: iron, nickel, molybdenum, and chromium on a quartz substrate using a gun sputtering deposition system using argon as sputtering gas. The catalysts were annealed at 200° C. for 24 hours in a vacuum oven at a pressure of $N_2$ around 10 torr. The catalysts were then loaded into a chemical vapor deposition reactor which was free of any volatile materials, pumped to high vacuum (less than about 1 torr) and the reactor was flushed with a mixture of high purity (greater than 99.9%) hydrogen and high purity argon wherein the argon and hydrogen were in a volume ratio of about 5:1. The flow rate was such that it took about 8 minutes to refresh the gas in the tube. The temperature was slowly ramped up from room temperature to 500° C. The catalysts were annealed for about 13 hours before ramping up to the temperature of 600° C. at 2° C. per minute under the same gas flow. The argon was switched off and replaced with a flow of ethylene. The volume ratio of ethylene to hydrogen was about 5:1. The catalysts were reacted for a half an hour before the ethylene source was shut off and replaced with argon. Under a constant flow of argon and hydrogen, the furnace was then turned off and allowed to cool to room temperature before the catalysts was taken out for analysis.

The catalysts were observed under a reflective optical microscope for the primary screen of catalyst candidates. Subsequently, scanning electron microscopy was used for secondary screening focusing on sample sites with adequate amount of carbon product. The following catalysts were shown to produce carbon fibrils by primary and secondary screening of the catalysts candidates: nickel and molybdenum; nickel and chromium; nickel, molybdenum and chromium; iron, nickel, and chromium; iron, nickel and molybdenum; and iron, nickel, molybdenum, and chromium.

EXAMPLE 2

Catalysts were fabricated with six metals: iron, cobalt, aluminum, zinc, chromium, and yttrium on a quartz substrate. Solutions of high purity metal nitrates were used as metal precursors (the concentration of all nitrate solutions used herein was 1 molar). Once the precursors were deposited on the substrate, the precursors were annealed at 200° C. for greater than 24 hours in a vacuum oven (pressure about 10 torr) to form catalysts. The catalysts were then loaded into a chemical vapor deposition reactor which was free of any volatile materials, pumped to high vacuum (less than 1 torr), and the reactor was flushed with a mixture of high purity (greater than 99.9%) hydrogen and high purity (greater than 99.9%) argon into the tube wherein the argon to hydrogen volume ratio was about 5:1. The flow rate was such that it took about 8 minutes to refresh the gas in the tube. The temperature was slowly ramped up from room temperature to 500° C. The catalysts were annealed for about 13 hours before ramping up the temperature to 600° C. at 2° C. per minute, under the same gas flow. Thereafter, the argon was switched off and replaced with a flow of ethylene. The volume ratio of ethylene to hydrogen was about 5:1. The catalysts reacted for about 30 minutes before the ethylene source was shut off and replaced with argon. Under a constant flow of argon and hydrogen, the furnace was then turned off and allowed to cool to room temperature before the catalysts were taken out for evaluation.

The catalysts were observed under a reflective optical microscope for the primary screen of catalyst candidates. A secondary screen was made using scanning electron microscopy (SEM) focusing on sample sites with adequate amount of carbon product. The following catalysts were determined as catalysts which produced carbon fibrils: nickel and iron; cobalt and iron; chromium and cobalt; zinc and cobalt; nickel and cobalt; nickel and chromium; nickel and zinc; nickel and copper; cobalt and copper; and nickel and aluminum.

EXAMPLE 3

Using the method of Example 2, catalysts were fabricated with eight metals: copper, iron, zinc, nickel, aluminum, cobalt, yttrium, and chromium on a quartz substrate. The following catalysts were shown to produce carbon fibrils: copper and iron; and aluminum and cobalt.

EXAMPLE 4

Using the method of Example 2, catalysts were fabricated with eight metals: copper, iron, zinc, nickel, aluminum, cobalt, yttrium, and chromium on a quartz substrate. The following catalysts produced carbon fibrils: cobalt, iron and copper; nickel, iron and yttrium; copper, iron, cobalt, and aluminum; cobalt and copper ; zinc, cobalt, chromium, and copper; yttrium, cobalt, nickel, and copper; cobalt, nickel and copper; nickel, chromium, and yttrium; cobalt, zinc and copper; zinc, yttrium, chromium, and nickel; aluminum, iron, and nickel; nickel, iron, yttrium, and aluminum; chromium and zinc; nickel and yttrium; and chromium, aluminum, and iron.

It is evident that with the vast array of elemental metals and metal alloys, there is a multitude of possible catalyst combinations. However, it was unexpectedly found that some iron combinations were ineffective catalysts for the production of carbon fibrils.

EXAMPLE 5

To form a catalyst, nickel (1 mole) and chromium (1 mole) were placed on an alumina substrate and were annealed at 200° C. for greater than 24 hours in a vacuum oven at a pressure around 10 torr in air. The catalyst was then loaded into a chemical vapor deposition reactor which was free of any volatile materials, pumped to high vacuum (less than about 1 torr) and the reactor was flushed with a mixture of high purity (greater than 99.9%) hydrogen and high purity (greater than 99.9%) argon wherein the argon to hydrogen were in a volume ratio of about 5:1. The gas flow was 6 cubic centimeters per second. The temperature was slowly ramped up from room temperature to 700° C. The argon was switched off and replaced with a flow of ethylene. The volume ratio of ethylene to hydrogen was about 5:1. The catalyst was reacted for 125 minutes before the ethylene source was shut off and replaced with argon. Under a constant flow of argon and hydrogen, the furnace was then turned off and allowed to cool to room temperature before the catalyst was taken out for analysis via scanning electron microscopy to verify carbon fibril growth. In addition, the net yield of carbon fibrils (the ratio of weight of carbon fibrils versus weight of metal catalyst) synthesized was 63.

EXAMPLE 6

The general procedure of Example 5 was followed where cobalt and chromium comprised the catalyst. In this example the mole ratio of cobalt to chromium was 2:1. The volume ratio of argon to hydrogen was initially 5.3 as was the volume ratio of ethylene to hydrogen. The gas flow was 8 cubic centimeters per second. The temperature of the reaction chamber was ramped up to 700° C. The reaction chamber was kept at 700° C. for 40 minutes. Scanning electron microscopy was used to verify carbon fibril growth. In addition, the net yield of carbon fibrils synthesized was 167.

EXAMPLE 7

The general procedure of Example 5 was followed where cobalt, zinc, and copper comprised the catalyst. The mole ratio of cobalt:zinc:copper was 2:0.4:1. The volume ratio of argon to hydrogen was initially 5:3 as was the volume ratio of ethylene to hydrogen. The gas flow was 8 cubic centimeters per second. The temperature of the reaction chamber was ramped up to 700° C. The reaction chamber was kept at 700° C. for 30 minutes. Scanning electron microscopy was used to verify carbon fibril growth. In addition, the net yield of carbon fibrils synthesized was 113.

EXAMPLE 8

The general procedure of Example 5 was followed where cobalt and copper comprised the catalyst. In this example, the mole ratio of cobalt to copper was 2:1. The volume ratio of argon to hydrogen was initially 5:3 as was the ratio of ethylene to hydrogen. The gas flow was 8 cubic centimeters per second. The temperature of the reaction chamber was ramped up to 700° C. The reaction chamber was kept at 700° C. for 30 minutes. Scanning electron microscopy was used to verify carbon fibril growth. In addition, the net yield of carbon fibrils synthesized was 133.

EXAMPLE 9

The general procedure of Example 5 was followed where cobalt, zinc, chromium, and copper comprised the catalyst. The mole ratio of cobalt:zinc:chromium:copper was 2:0.4:1:1. The volume ratio of argon to hydrogen was initially 5:3 as was the volume ratio of ethylene to hydrogen. The gas flow was 8 cubic centimeters per second. The temperature of the reaction chamber was ramped up to 700° C. The reaction chamber was kept at 700° C. for 30 minutes. Scanning electron microscopy was used to verify carbon fibril growth. In addition, the net yield of carbon fibrils synthesized was 33.

EXAMPLE 10

The general procedure of Example 5 was followed where cobalt, nickel and copper comprised the catalyst. In this example the mole ratio of cobalt:nickel:copper was 1:1:2. The volume ratio of argon to hydrogen was initially 5:3 as was the volume ratio of ethylene to hydrogen. The gas flow was 8 cubic centimeters per second. The temperature of the reaction chamber was ramped up to 700° C. The reaction chamber was kept at 700° C. for 30 minutes. Scanning electron microscopy was used to verify carbon fibril growth. In addition, the net yield of carbon fibrils synthesized was 96.

EXAMPLE 11

The general procedure of Example 5 was followed where nickel, iron and yttrium comprised the catalyst. In this example, the mole ratio of nickel:iron:yttrium was 1:1:1. The volume ratio of argon to hydrogen was initially 5:3 as was the ratio of ethylene to hydrogen. The gas flow was 8 cubic centimeters per second. The temperature of the reaction chamber was ramped up to 700° C. The reaction chamber was kept at 700° C. for 30 minutes. Scanning electron microscopy was used to verify carbon fibril growth. In addition, the net yield of carbon fibrils synthesized was 20.

While typical embodiments have been set forth for the purpose of illustration, the foregoing descriptions should not be deemed to be a limitation on the scope of the invention. Accordingly, various modifications, adaptations, and alternatives may occur to one skilled in the art without departing from the spirit and scope of the present invention as defined by the following claims.

What is claimed is:

1. A catalyst system for making carbon fibrils, the system comprising a catalytic amount of an inorganic catalyst comprising nickel and one of the following substances selected from the group consisting of chromium; chromium and iron; chromium and molybdenum; chromium, molybdenum, and iron; aluminum; yttrium and iron; yttrium, iron and aluminum; zinc; copper; yttrium; yttrium and chromium; and yttrium, chromium and zinc;

wherein the catalyst system is supported on a quartz substrate.

2. The system of claim 1, wherein the inorganic catalyst comprises nickel and chromium.

3. The system of claim 2, wherein the inorganic catalyst further comprises iron.

4. The system of claim 2, wherein the inorganic catalyst further comprises molybdenum.

5. The system of claim 4, wherein the inorganic catalyst further comprises iron.

6. The system of claim 2, wherein the inorganic catalyst further comprises yttrium.

7. The system of claim 6, wherein the inorganic catalyst further comprises zinc.

8. The system of claim 1, wherein the inorganic catalyst comprises nickel and aluminum.

9. The system of claim 1, wherein the inorganic catalyst comprises nickel and yttrium.

10. The system of claim 9, wherein the inorganic catalyst further comprises iron.

11. The system of claim 10, wherein the inorganic catalyst further comprises aluminum.

12. The system of claim 1, wherein the inorganic catalyst comprises nickel and zinc.

13. The system of claim 1, wherein the inorganic catalyst comprises nickel and copper.

14. The system of claim 1, wherein the inorganic catalyst is substantially free of iron.

* * * * *